(12) United States Patent
Momberger et al.

(10) Patent No.: US 6,436,438 B1
(45) Date of Patent: *Aug. 20, 2002

(54) TRAMADOL MULTIPLE UNIT FORMULATIONS

(75) Inventors: Helmut Momberger, Marburg; Marc Raber, Giessen; Dieter Kuhn, Marburg; Wolfgang Schmid, Lohra, all of (DE)

(73) Assignee: Asto-Medica AG, Radebeul (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/349,564

(22) Filed: Jul. 8, 1999

Related U.S. Application Data

(62) Division of application No. 08/896,629, filed on Jul. 18, 1997, now Pat. No. 5,955,104.

(30) Foreign Application Priority Data

Jul. 25, 1996 (DE) .......................... 196 30 035

(51) Int. Cl.[7] .............. A61K 9/22; A61K 9/54; A61K 9/60; A61K 9/62
(52) U.S. Cl. ............... 424/458; 424/457; 424/459; 424/461; 424/462; 424/468; 424/494; 424/495; 424/496; 424/497; 514/770; 514/781; 514/782; 514/951
(58) Field of Search ................ 424/472, 458, 424/459, 461, 462, 494, 495, 497, 457, 468, 496, 456, 469, 470

(56) References Cited

U.S. PATENT DOCUMENTS 5,026,560 A * 6/1991 Makino et al. ............ 424/494
5,344,657 A * 9/1994 Desmolin ................. 424/458
5,478,577 A * 12/1995 Sackler et al. ............. 424/489
5,567,441 A * 10/1996 Chen ....................... 424/494
5,955,104 A * 9/1999 Momberger et al. ........ 424/458

* cited by examiner

Primary Examiner—James M. Spear

(57) ABSTRACT

A multiple unit oral pharmaceutical dosage form having a plurality of pellets in a water soluble capsule or in a tablet compressed from the pellets, wherein each pellet contains (a) a substantially inert core, (b) an active ingredient layer over the inert core, and containing (i) a pharmacologically active particulate active ingredient, (ii) a nonembedding amount of a binder for adhering the active ingredient over the inert core, and optionally (iii) a pharmaceutically acceptable, inert adjuvant, such as colloidal silica, and (c) a coating over the active ingredient layer for retarding the release of the active ingredient from the active ingredient layer into an aqueous body fluid solvent in situ, the nonembedding amount of the binder is suitably from about 1% wt. to about 10% wt. based on the active ingredient layer, the binder in the active ingredient layer is suitably a mixture of ethylcellulose and shellac, in a weight proportion suitably of from about 1: about 9, to from about 9: about 1, the coating for retarding the release suitably contains from about 70% wt. to about 95% wt. based on the coating, of a substantially water-insoluble, pharmacologically inert, particulate material, and a binder; the pharmacologically inert, particulate material is suitably talcum, and the binder in the active ingredient layer is suitably identical to the binder in the coating.

20 Claims, 7 Drawing Sheets

TRAMADOL MULTIPLE UNIT FORMULATIONS

This application is a Divisional of Ser. No. 08/896,629 filed Jul. 18, 1997 now U.S. Pat. No. 5,955,104.

FIELD OF THE INVENTION

The invention relates to oral, multiple unit formulations of delayed-release pellets which contain a pharmacologically active component coated by at least one pharmaceutically acceptable, release-delaying substance, and to a process for their preparation.

BACKGROUND

Single unit controlled release tablet dosage forms of drugs have known disadvantages compared to the more desirable multiple unit dosage forms. In single dosage matrix tablets the active ingredient is dispersed as a solid in an inert, release delaying matrix. The embedding matrixing material that slows the release of the drug is usually an insoluble plastic (e.g. methyl acrylate-methacrylate, polyvinyl chloride, or polyethylene), a hydrophilic polymer (e.g. methylcellulose, hydroxypropylmethylcellulose, or sodium carboxyl methylcellulose), or fatty compounds (e.g. various waxes, such as carnauba wax, or glyceryl stearate). Such tablets pass undisintegrated through the gastrointestinal tract, and become ever smaller due to breakdown (erosion tablets), or wherein the active compound is released only in the intestine (enteric-coated tablets), in either case depleting the surface inward through the matrix by dissolution or diffusion through the matrix to the external solution.

Multiple unit dosage forms are usually contained within a rapid dissolving capsule, or are compressed into a tablet, and soon after ingestion upon its dissolution fall apart into the multiple units, such as pellets. The sub-units or pellets have the desired slow release properties of the dosage form. In contrast to the matrixed formulations, the multiple unit pellets are each surrounded by a polymeric delay release film coating that provides the controlled, slowed release of the active ingredient from within the pellet. These coated dosage forms are generally referred to as "reservoir devices" when diffusion phenomena occur through the release slowing coat, or "encapsulated formulations" when the slow release coat slowly dissolves (see e.g. Remington's Pharmaceutical Sciences, Mack Publ. Co.). In the case of the single unit, matrixed delayed-release dosage forms, considerable variations can occur in the gastric residence times, and this can lead to an irregular passage through the gastrointestinal tract and thus to differing, fluctuating blood level values. Local irritation is also becomes of lesser concern also being reduced by the use of multiple unit pharmaceutical dosage forms. "Dose dumping" or the too rapid release of the active compound from delayed-release dosage forms (see e.g. H. Blume, "Biopharmazeutische Aspekte von Multiple Unit Dosage Forms; ein Vergleich mit Single Units" [Biopharmaceutical aspects of multiple unit dosage forms; a comparison with single units], published by Capsugel, Basel, and delivered at a symposium in November 1988 in Hamburg).

A variety of pharmaceutical formulations having delayed-release coatings are described, for example, in EP No. 147,780, in the form of tablets and granules which contain an active compound core and are coated with a film of polyvinyl alcohol.

In EP No. 634,366 an oral dosage form for delayed release tramadol preparations is disclosed wherein the active compound is either embedded in a delayed-release matrix of hydrophilic or hydrophobic polymers, long-chain fatty acids or fatty alcohols and one or more polyalkylene glycol. Film-coated spheroids are also described in which the active ingredient is embedded in a "spheronizing" material, such as in microcrystalline cellulose, and coated with a release controlling film.

In EP No. 731,694 (WO95/14460) delayed-release opioid formulations, for example pellets, are described which provide an analgesic effect over at least 24 hours after oral administration. The pellets have of an active ingredient-containing core which is covered with a polymer film suitable for delaying the release of the active. In addition to the polymers the film contains an acid-soluble compound and a plasticizer. The use of plasticizers, however, can be most disadvantageous, because these migrate out of the membrane, and this composition change can affect the release of active compound during storage. EP No. 147 780 describes on page 2 that a chemical interaction between plasticizer and the active compound can also take place and this leads to a reduction in the shelf life of the product.

It is mentioned in Sucker, Fuchs, Speiser "Pharmazeutische Technologie" Thieme Verlag Publisher. Stuttgart, 1978, that beside its actual film-improving property, the plasticizer affects water vapor permeability and the disintegration. The admittedly low but noticeable vapor pressure furthermore leads to an evaporation of the plasticizer, resulting in an alteration of the physical properties, such as the dissolution rate of the film.

Pellet formulations are distinguished by their large surface area because of the presence of many, often a few hundred sub-units per therapeutic dose. In the case of readily soluble substances such as tramadol hydrochloride, this can lead to a need for delayed release material, which undesirably reduces the active ingredient content of the pellet formulation. This is particularly undesirable in the case of actives which are administered at relatively high doses, because the quantity of pellets necessitates the use of a larger hard gelatine capsule. This is therapeutically undesirable, because it can be unpleasant for the patient.

SUMMARY DESCRIPTION OF THE INVENTION

The present invention is a multiple unit oral pharmaceutical dosage form having a plurality of pellets in a water soluble capsule or in a tablet compressed from the pellets, wherein each pellet contains (a) a substantially inert core, (b) an active ingredient layer over the inert core, and containing (i) a pharmacologically active particulate ingredient, (ii) a nonembedding amount of a binder for adhering the active ingredient over the inert core, and optionally (iii) a pharmaceutically acceptable, inert adjuvant, such as colloidal silica, and (c) a coating over the active ingredient layer for retarding the release of the active ingredient from the active ingredient layer into an aqueous body fluid solvent in situ. Suitably the nonembedding amount of the binder is from about 1% wt. to about 10% wt. based on the active ingredient layer. Suitably the binder in the active ingredient layer is a mixture of ethylcellulose and shellac, suitably in a weight proportion of from about 1:9, to from about 9:1. The coating for retarding the release suitably contains from about 70% wt. to about 95% wt. based on the coating, of a substantially water-insoluble, pharmacologically inert, particulate material, and a binder. Suitably the pharmacologically inert, particulate material is talcum, and the binder in the active ingredient layer is suitably identical to the binder in the coating.

As used throughout the specification and the claims, the term "active" and "active ingredient" means any pharmacologically active material that is suitable for use in reservoir type or in encapsulated type, i.e. nonmatrixed dosage forms. Thus the choice of the active employed in the dosage form of the present invention is a noncritical feature, wherein the active can suitably be an antiinflammatory, such as aspirin, diclofenac, ibuprofen, acetaminophen, indomethacin, ketoprofen, and hydrocortisone; an antiemetic, such as metoclopramide, and domperidon; an antihypertensive, such as clonidine, captopril, atenolol and propranolol; an opioid analgesic such as codeine, dihydrocodeine, hydrocodone, hydromorphone, morphine, oxycodone, fenantyl, tramadol, tilidin, and tilidin-naloxone combination; a nonopioid analgesic, such as paracetamol, aspirin, ibuprofen, acetaminophen, dipyrone, ketoprofen, naproxene, and flupirtine; an antiasthmatic, such as theophylline, and azelastine; an antiepileptic, such as carbamazepine, and phenytoin; and an H2 antagonist, such as ranitidine, and cimetidine; and pharmaceutically acceptable salts and esters of the above. Most suitably the active ingredient is tramadol or a pharmaceutically acceptable salt or ester thereof.

As used throughout the specification and the claims, reference to a nonembedding amount of binder means that the vast majority of the active ingredient layer is the active ingredient itself, and only so little binder is present that the active ingredient is not embedded in any embedding material or matrix of any kind, but under a microscope it visibly retains its particulate identity. The active ingredient layer is applied over the inert core by spraying it, or a solution thereof, onto the core, together with a small amount of the binder in a solution. It can be seen under a microscope that the binder solution does not coat or embed the active ingredient particles, but they visibly retain their particulate integrity. It has been found that the amount of binder in solution that will not fully wet the particles of the active ingredient, but will still permit their bonding to the inert core and to each other, is suitably between from about 1% wt. to about 10% wt. based on the active ingredient layer. The optimum concentration of the binder will generally depend within that range on such factors as the identities of the solvent of the binder, the method of spraying the solution on the active, any solvent for the active and its evaporation rate upon the application of the active, and the particle size and surface characteristics, such as specific solvent wettability of the active ingredient and any other particulate adjuvant that may be used therewith. All of these variables can be routinely tested and optimized by persons having average skill in the pharmaceutical formulation art.

Any reference throughout the specification and the claims to water solubility of any material in the dosage form of the present invention, and to release of the active ingredient into a solvent medium, include solubility within the aqueous biological solvent in the body of a patient at the site or sites at which the dosage form is to release its active ingredient content.

BRIEF DESCRIPTION OF THE DRAWINGS

The present invention is explained in greater detail, with reference being had to the drawing, wherein.

DETAILED DESCRIPTION

Figure 1:
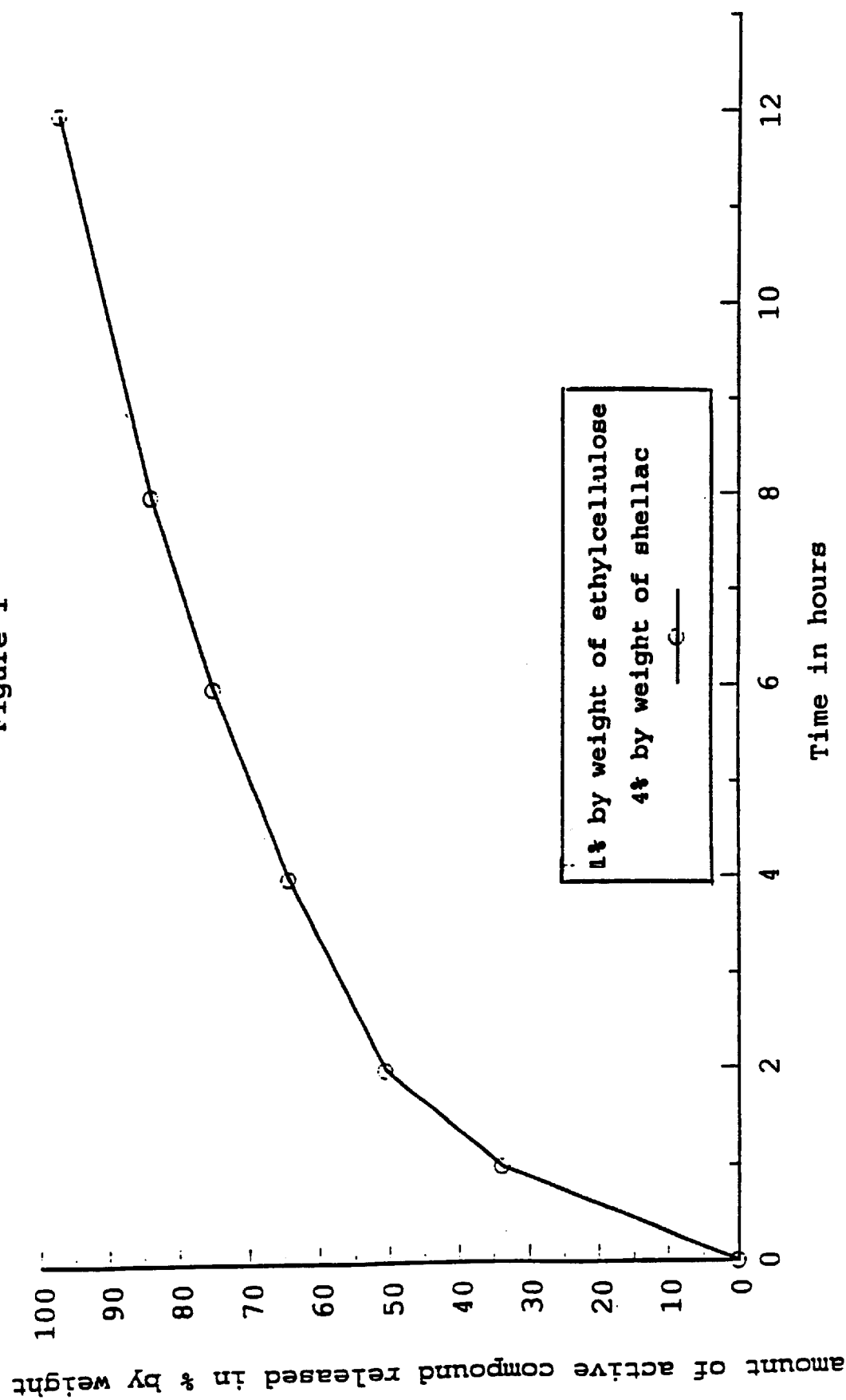
FIGS. 1–6 show 12 hour release rate profiles of multiple unit delayed release tramadol dosage forms using various kinds of binder components in the active ingredient layer in accordance with the present invention.
Figure 2:
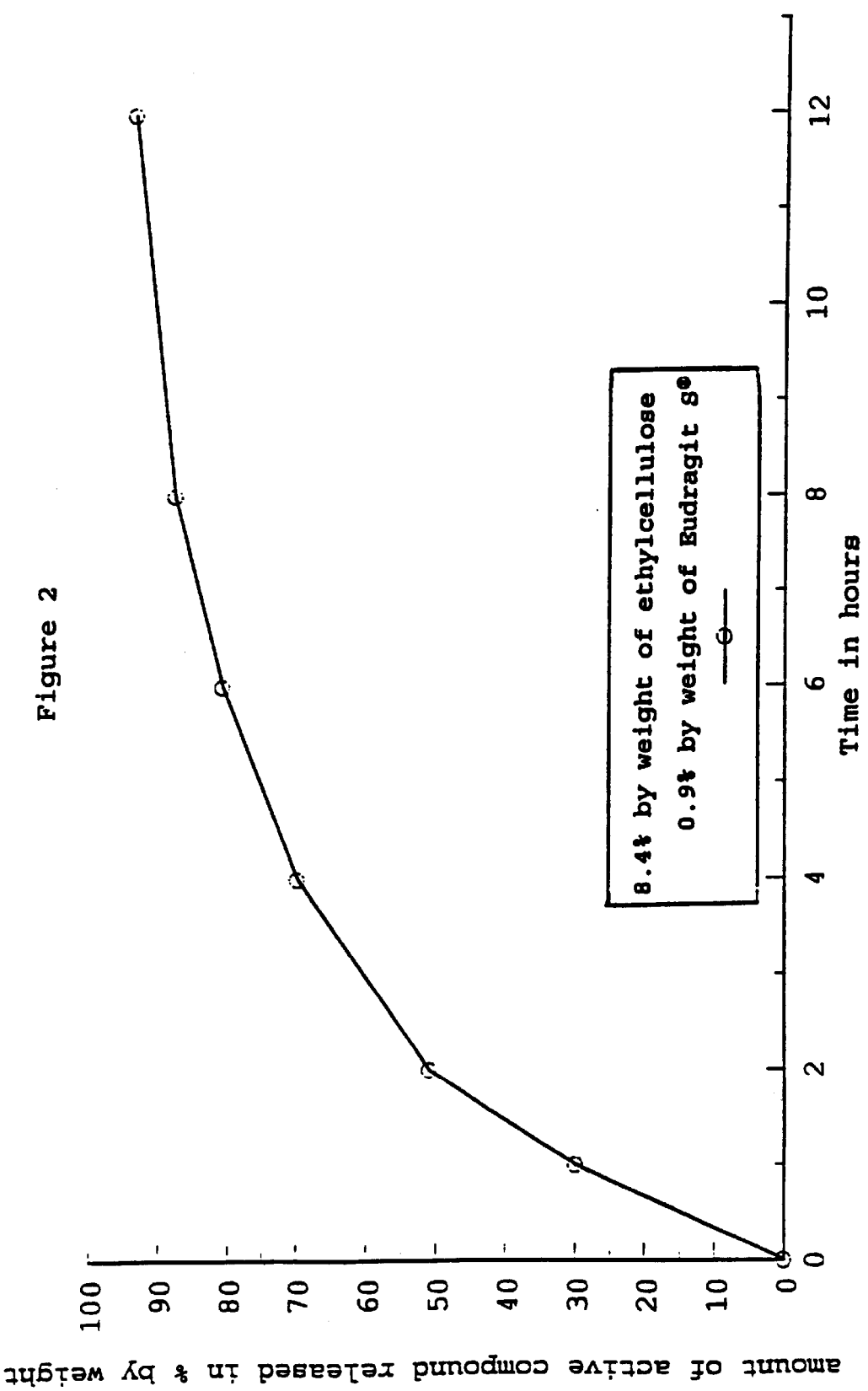
Figure 3:
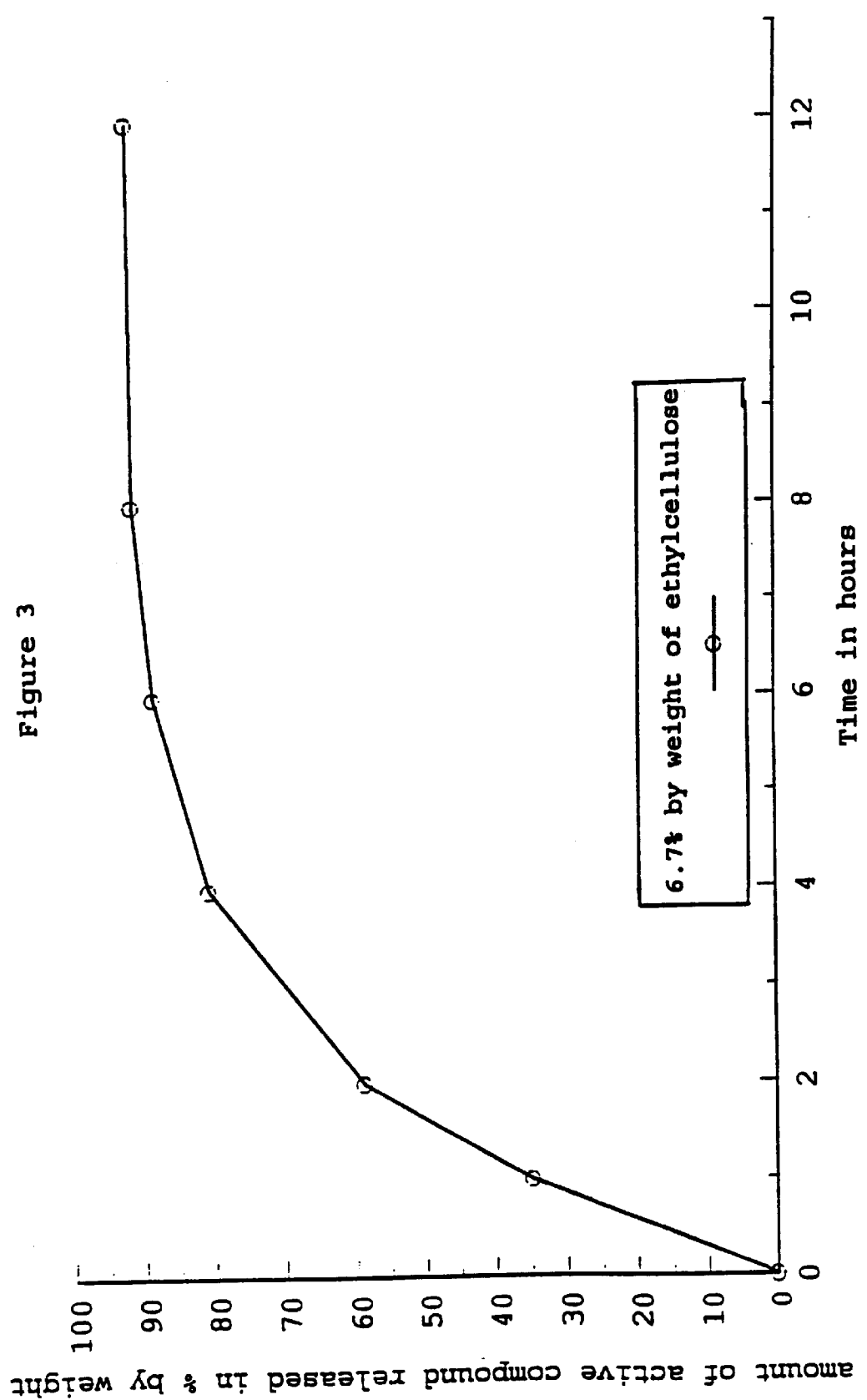
Figure 4:
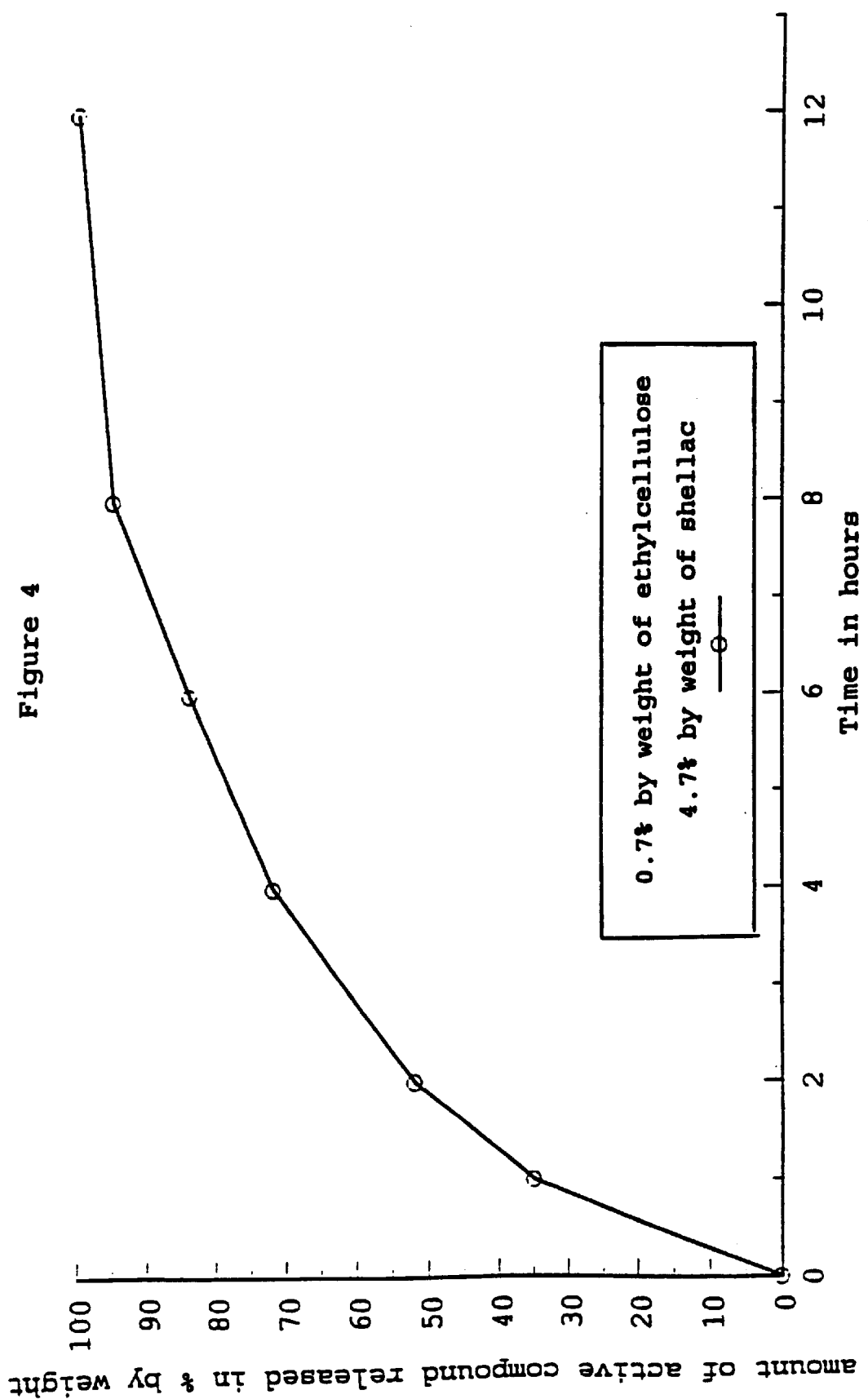
Figure 5:
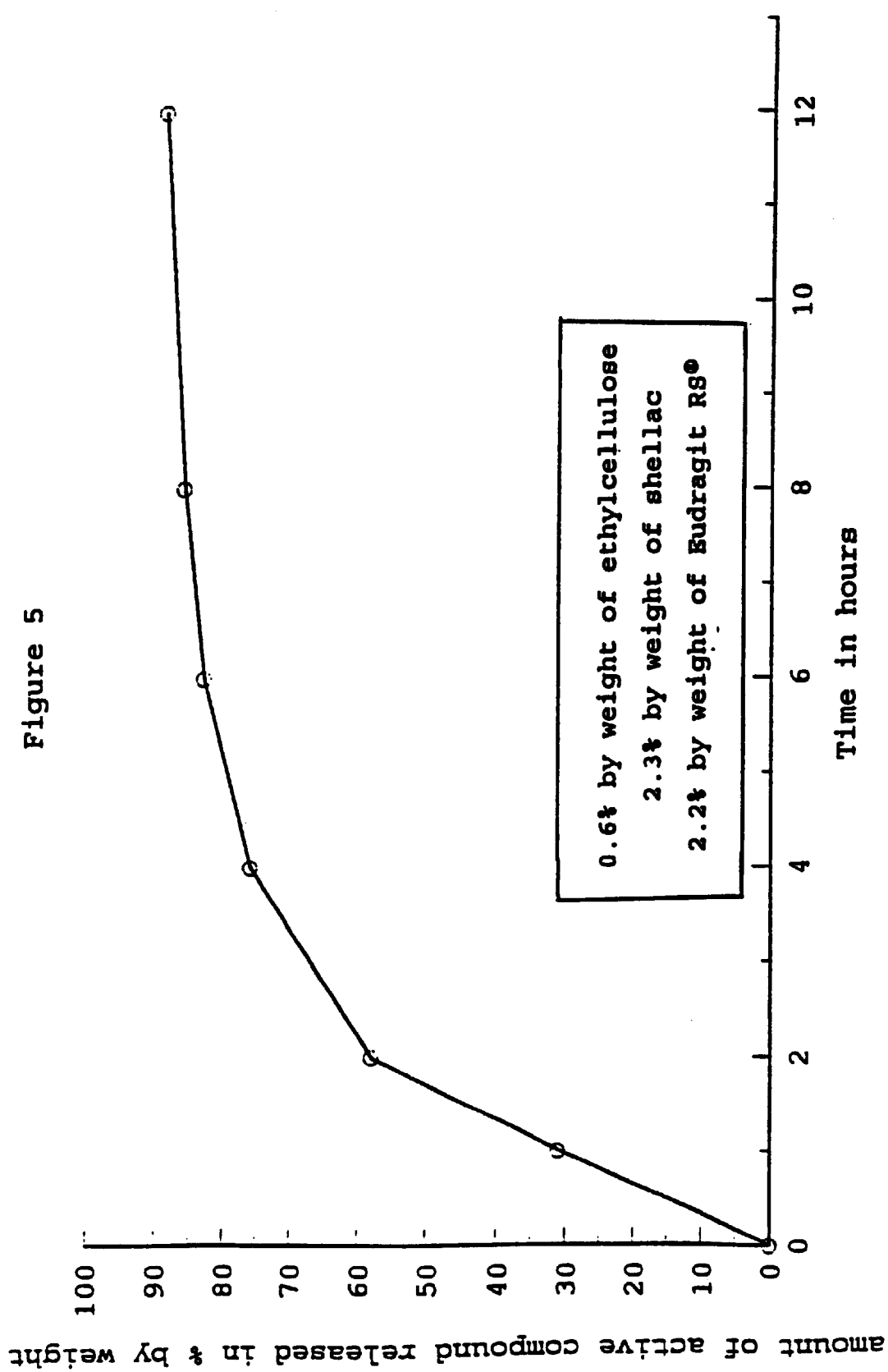
Figure 6:
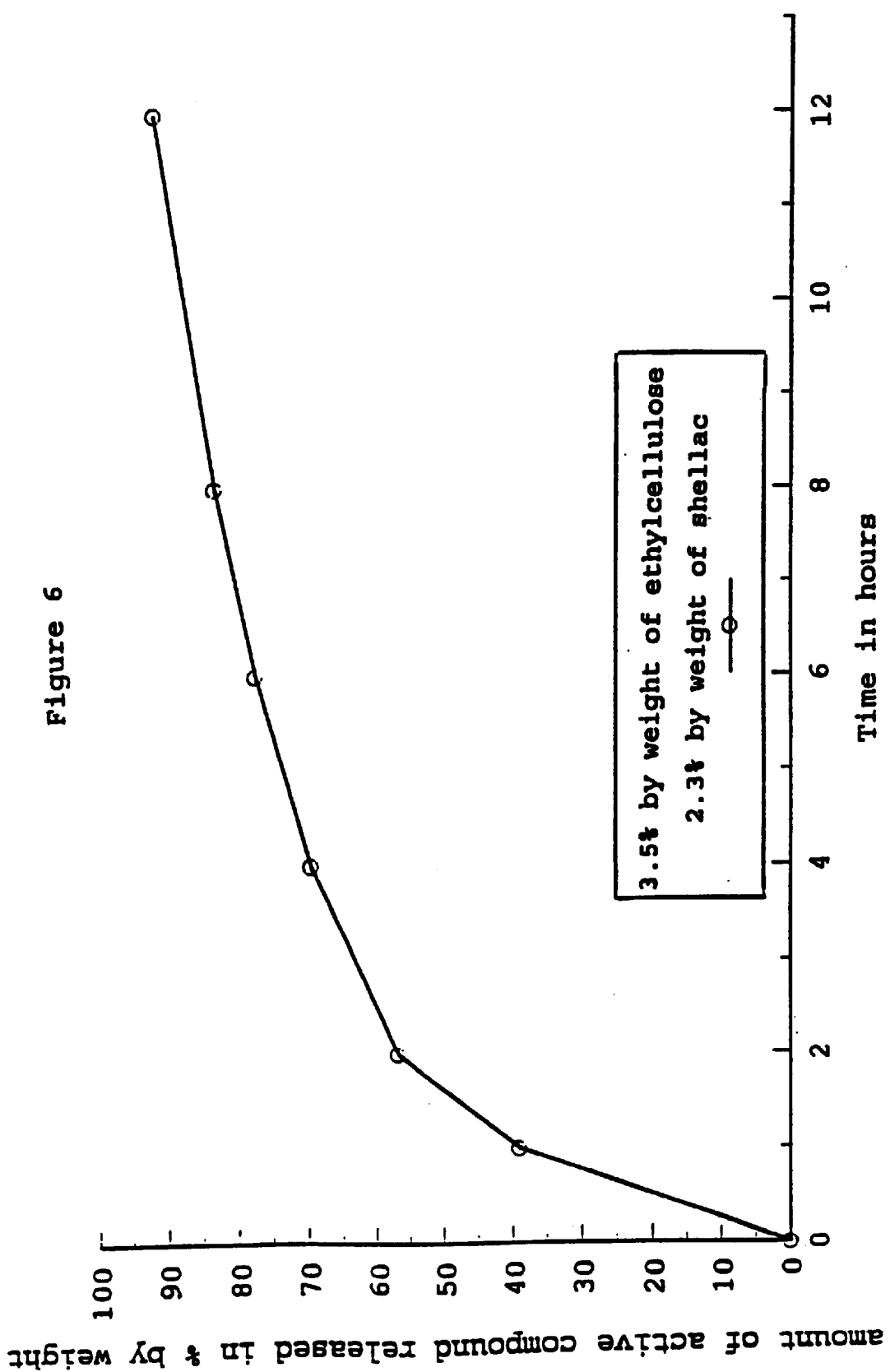
Figure 7:
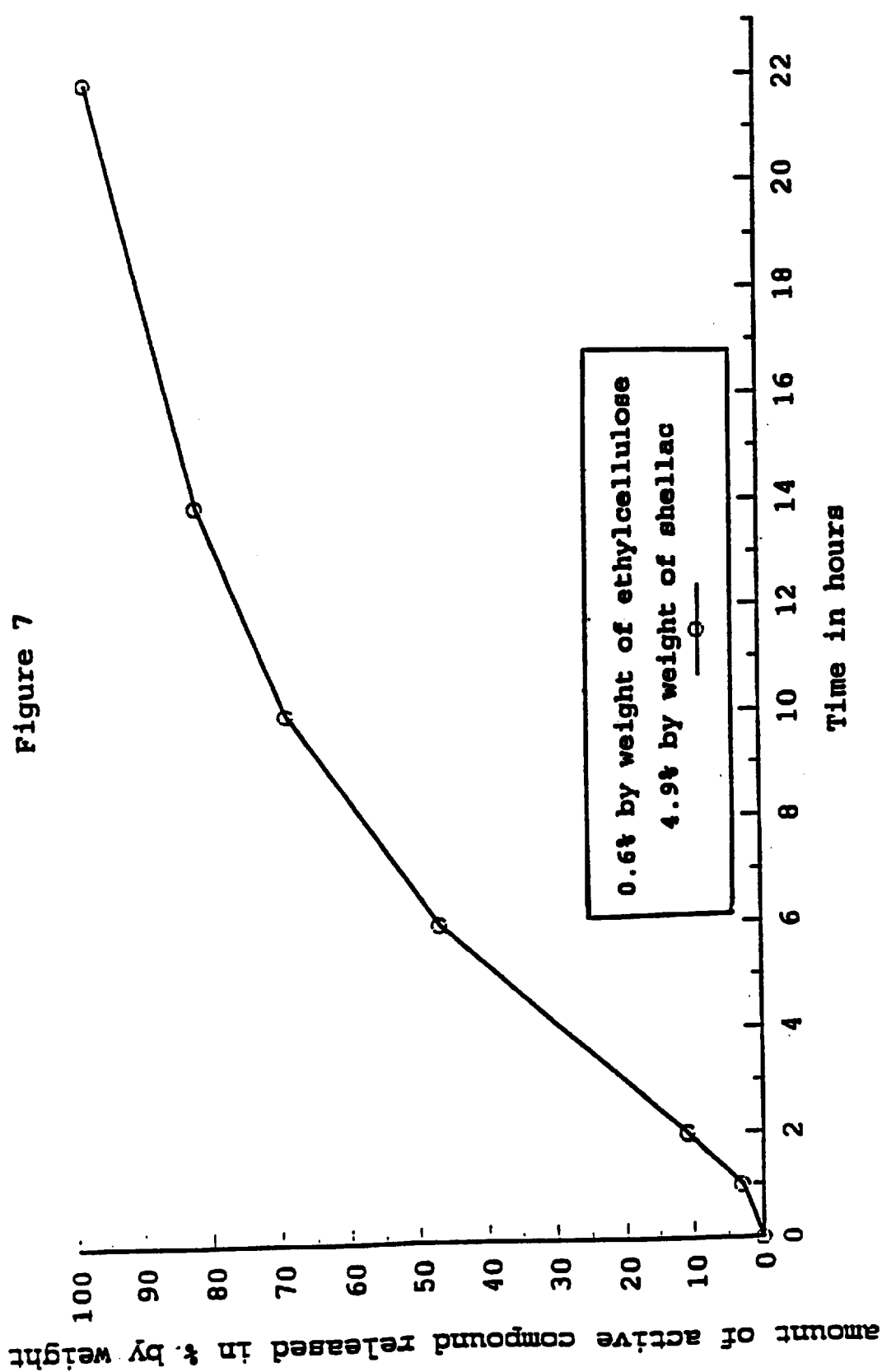
FIG. 7 shows a 24-hour release rate profile of a tramadol dosage form of the present invention.

The active ingredient can be applied to the inert case by itself, or in admixture with materials, such as colloidal silica to improve the processing of the active.

The pellet core is suitably an inert starter material, over which the active compound is applied in a suitable solvent. One can employ as a starter material for pellet preparation, for example sucrose crystals or alternatively sucrose-maize starch pellets (nonpareils, neutral pellets, sugar spheres USP 23/NF 18).

On account of the good solubility of the active ingredient, lower alcohols such as ethanol, isopropanol and alcohol/water mixtures, or acetone can be used as a solvent to apply the active over the inert core. The process can be accelerated by simultaneously applying the active compound in powder form and also in dissolved form, or by using solutions alone.

Suitably the particulate active compound is applied to the inert core by spraying into a pan together with the required small amount of a suitable binding agent solution. This application of the active compound can be carried in multiple layers so that if desired, the process can be interrupted for a longer or shorter time, suitably with an intermediate drying/evaporation of the solvent between the layering sprays.

Regardless of whether the active ingredient is applied from an aqueous solution, as a particulate solid, or as a mixture of a solution and a solid, by the time the spray contacts the inert core the active is in a solid form.

Only sufficient binding agent solution, which can contain a binding agent or a combination of several binding agents, is employed so that the active compound becomes attached to the core and also to adjacent active particles. The active compound layer thus mainly contains the active compound itself and only up to about 10% wt. or less of one or more of the binding agents (dry basis).

The binder in the active ingredient layer and/or in the delay coating can suitably be one or more of a polyvinylpyrrolidone, such as sold by E.I. Dupont Co. under the trade name PVP 25, a hydrophilic cellulose ether, such as hydroxypropylmethyl-cellulose, ethylcelluloses of various degrees of ethylation and of various chain lengths, shellac, anionic copolymers of methacrylic acid and methyl methacrylate or ethyl acrylate, such as methacrylic acid copolymer type A, B and C describe in USP 23/NF 18, for example as sold under the trade names as Eudragit L®, Eudragit S® and Eudragit L 100-55®, ammonia methacrylate copolymer type A and B, sold for example as Eudragit RL® and Eudragit RS®, cellulose acetate phthalate and hydroxypropylmethylcellulose acetate phthalate.

Depending on binder solubilities, suitably water, or lower alcohols such as ethanol, isopropanol, alcohol/water mixtures or acetone can be used as solvents for the binders in the active layer as well as in the delay coat.

The release-delaying substances can be processed separately or in combination with one another. Suitably a mixture of ethylcellulose with shellac is employed, most suitably in a ratio of from about 1:9 to about 9:1. Likewise, combinations of ethylcellulose with Eudragit S® are also suitable.

A particularly preferred embodiment of the present invention employs the same kind of mixture of ethylcellulose and shellac both in the active ingredient layer and in the delay coating. The use of the same polymers for the bonding of the active compound to the inert core, and also in the delayed release coat, pellets of particularly simple composition are obtained, which are easy to prepare, have more easily predictable release characteristics, and contain only a few different ingredient and are thus of great advantage to the patient.

Further adjuvants can be employed in the active ingredient layer and/or the controlled release coat, such as ingredients that are customary pharmaceutical auxiliary materials or adjuvants, such as release agents and flow-regulating agents, for example colloidal silica, talc, and magnesium stearate. Talc has a particularly beneficial role in the controlled release coat of the present invention, also enabling the use of a minimal amount of the polymeric binder in that coat.

The pellets can be optionally designed to offer varying dissolution profiles delay by applying different delay coatings, or delay coatings of varying thickness with various release delaying agents, this affording further alternatives for the control of the release of the active compound.

These multiple unit pellet formulations delayed to an identical or to a different extent pass continuously through the pylorus, even in its closed state, and are dispersed through the entire gastrointestinal region. This leads to a very uniform passage through and absorption from the gastrointestinal tract.

The pellets are prepared by generally customary pelletizing methods, such as described in Pharmaceutical Pelletization Technology, edited by Isaac Ghebre-Sellassie, Marcel Dekker Publisher, 1989.

We claim:

1. A multiple unit oral pharmaceutical dosage form, which comprises a plurality of pellets in a water soluble capsule or in a tablet compressed from said pellets, each pellet having
   (a) a substantially inert core;
   (b) an active ingredient layer over said inert core, and containing (i) a pharmacologically active particulate active ingredient, (ii) a nonembedding amount of from about 1% to about 10% wt. based on the active ingredient layer of a binder for adhering said active ingredient over said inert core, and optionally (iii) a pharmaceutically acceptable, inert adjuvant; and
   (c) an identical kind of delay coating on each pellet for retarding the release of said active ingredient.

2. The dosage form of claim 1, wherein said binder in said active ingredient layer is a water insoluble polymer.

3. The dosage form of claim 1, wherein said binder in said active ingredient layer is a mixture of ethylcellulose and shellac.

4. The dosage form of claim 2, wherein said ethylcellulose and shellac are present in a weight proportion of from about 1:9 to about 9:1.

5. The dosage form of claim 1, wherein said delay coating comprises from about 70% wt. to about 95% wt. based on the delay coating, of a substantially water-insoluble, pharmacologically inert, particulate material, and a binder.

6. The dosage form of claim 4, wherein said substantially water-insoluble, pharmacologically inert, particulate material is talcum.

7. The dosage form of claim 1, wherein said binder in said active ingredient layer, and said binder in said delay coating are substantially identical.

8. The dosage form of claim 1, wherein said active ingredient is one or more of an antiinflammatory, an antiemetic, an antihypertensive, an opioid analgesic, a non-opioid analgesic, an antiasthmatic, an antiepileptic, and an H2 antagonist.

9. The dosage form of claim 7, wherein said active ingredient is tramadol.

10. The dosage form of claim 1, wherein said substantially inert core is a sucrose or nonpareil material.

11. The dosage form of claim 1, wherein the binder in said active ingredient layer is one or more of polyvinylpyrrolidone, hydrophilic cellulose ether, ethylcellulose, shellac, anionic methacrylic acid/methacrylate copolymer, cellulose acetate phthalate, and hydroxypropylmethylcellulose.

12. The dosage form of claim 10, wherein the binder in said active ingredient layer is substantially the same as the binder in said delay coating.

13. The dosage form of claim 1, wherein said optional adjuvant in said active layer is a release agent or a lubricant.

14. The dosage form of claim 12, wherein aid adjuvant is one or more of colloidal silica, magnesium stearate, and talcum.

15. The dosage form of claim 1, further comprising a small amount of active deposited on the exterior of the delay coating of a pellet, for instant availability to the host organism upon ingestion.

16. The dosage form of claim 1, wherein the average diameter of the pellets in said dosage form is between about 0.4 mm and about 3.0 mm.

17. The dosage form of claim 15, wherein said diameter is between about 0.6 mm and about 1.6 mm.

18. The dosage form of claim 1, when the pellets are contained in a capsule, the capsule providing either a 24 hour release rate profile, or a 12 hour bidcap release rate profile.

19. A process for preparing the dosage form of claim 1, which comprises applying in one or more layers the active ingredient and a nonembedded amount of a solution of the binder for the active ingredient layer over an inert, particulate core, and applying over said active-coated core a solution of the same kind of a delayed release coating on all pellets, said delayed release coating containing a binder in a solution, wherein the binder is optionally identical to the binder used as a binder in the active layer, and optionally further coating a non-delayed layer of the active ingredient onto the delayed release coating, before encapsulating the pellets or compressing them into a tablet.

20. The process of claim 19, wherein said step of applying the active ingredient onto the inert core comprises (i) spraying a solution of the active ingredient, or (ii) spraying the active ingredient in a particulate form admixed with the binder solution.

* * * * *